United States Patent
Isenberg et al.

(10) Patent No.: US 9,714,588 B2
(45) Date of Patent: Jul. 25, 2017

(54) OIL RECIRCULATION SYSTEM FOR ENGINES

(71) Applicant: Caterpillar Inc., Peoria, IL (US)

(72) Inventors: Walter S. Isenberg, Frankfort, IN (US); Kevin P. Storms, Darlington, IN (US)

(73) Assignee: Caterpillar Inc., Peoria, IL (US)

( * ) Notice: Subject to any disclaimer, the term of this patent is extended or adjusted under 35 U.S.C. 154(b) by 196 days.

(21) Appl. No.: 14/793,798

(22) Filed: Jul. 8, 2015

(65) Prior Publication Data
US 2017/0009619 A1   Jan. 12, 2017

(51) Int. Cl.
| | |
|---|---|
| F01M 1/10 | (2006.01) |
| F01M 11/03 | (2006.01) |
| F01M 11/10 | (2006.01) |
| F01M 11/02 | (2006.01) |
| G01N 33/28 | (2006.01) |
| F02B 63/04 | (2006.01) |

(52) U.S. Cl.
CPC .............. F01M 1/10 (2013.01); F01M 11/02 (2013.01); F01M 11/03 (2013.01); F01M 11/10 (2013.01); G01N 33/2835 (2013.01); F01M 2001/1028 (2013.01); F02B 63/04 (2013.01); F16N 2200/04 (2013.01)

(58) Field of Classification Search
CPC .......... F01M 1/10; F01M 11/02; F01M 11/03; F01M 11/10; F01M 2001/1028; F16N 2200/04; G01N 33/2835
See application file for complete search history.

(56) References Cited

U.S. PATENT DOCUMENTS

| | | | | |
|---|---|---|---|---|
| 2,262,526 | A * | 11/1941 | Beare | C10M 175/0091 123/196 A |
| 3,502,970 | A * | 3/1970 | Thayer | B01D 35/143 324/669 |
| 3,878,103 | A * | 4/1975 | Miller | G01N 15/0618 174/117 M |

(Continued)

FOREIGN PATENT DOCUMENTS

CA      2741797       11/2012

OTHER PUBLICATIONS

T.M. Hunt, Handbook of Wear Debris Analysis and Particle Detection in Liquids, book, p. 302.

*Primary Examiner* — William E Dondero
*Assistant Examiner* — Robert T Reese

(57) ABSTRACT

An oil recirculation system for an engine is disclosed. The oil recirculation system includes a first conduit coupled to the engine to receive an oil and a second conduit coupled to the engine to supply the oil to the engine. The oil recirculation system further includes a filtering device disposed between the first and second conduits. The filtering device includes a first housing member defining a first chamber therein. The first chamber is in fluid communication with the first conduit. The filtering device further includes a second housing member removably coupled to the first housing member and defines a second chamber therein. The second chamber is in fluid communication with the second conduit. The first and second chambers together define a passage to receive the oil therethrough. The filtering device further includes a filter member disposed in the passage to filter the oil flowing therethrough.

20 Claims, 3 Drawing Sheets

(56) References Cited

U.S. PATENT DOCUMENTS

| | | | |
|---|---|---|---|
| 4,176,545 A | 12/1979 | Oddo | |
| 5,608,315 A | 3/1997 | Crayton et al. | |
| 6,453,738 B1* | 9/2002 | Cesmat | B01D 21/0009 |
| | | | 166/265 |
| 6,582,661 B1 | 6/2003 | Pardue et al. | |
| 8,795,522 B2 | 8/2014 | Unger et al. | |
| 2002/0185454 A1* | 12/2002 | Beard | B01D 27/005 |
| | | | 210/749 |
| 2004/0140255 A1* | 7/2004 | Merritt | B01D 29/15 |
| | | | 210/232 |
| 2004/0154970 A1* | 8/2004 | Rohrbach | B01D 27/02 |
| | | | 210/266 |
| 2014/0251883 A1* | 9/2014 | Saito | F01M 11/03 |
| | | | 210/167.02 |
| 2014/0305740 A1 | 10/2014 | McCollough et al. | |
| 2016/0223469 A1* | 8/2016 | Horstmeyer | F16N 29/00 |

\* cited by examiner

OIL RECIRCULATION SYSTEM FOR ENGINES

TECHNICAL FIELD

The present disclosure relates to an oil recirculation system for an engine, and more particularly relates to a filtering device disposed in the oil recirculation system.

BACKGROUND

Engine uses lubrication oil for lubricating various moving components, such as a crankshaft, camshafts and pistons, to avoid wear and also to serve as a cooling medium by absorbing heat from such components. The lubrication oil is contained in an oil pan and supplied to the components by an oil pump during operation of the engine. One or more filters are also disposed in the oil pan to filter the lubrication oil. After a prolonged period of operation of the engine, impurities present in lubrication region and wear particles formed due to friction of mating components may be added in the lubrication oil. Excessive amount of such wear particles and the impurities may damage the components and reduce efficiency of the engine. Hence, the customer may periodically inspect the lubrication oil for assessing extent of wear particles in the oil. However, taking a volume of the lubrication oil from the engine and assessing an extent of wear particles in the oil needs more time. Also, inspection of quality of the oil is a complex process.

U.S. Pat. No. 4,176,545 discloses an apparatus and electrical system for sensing wear within an engine by detecting the presence of metal pieces which have become dislodged from the engine. The metal pieces are detected by collecting them upon a filter which is located generally within an inductor. The permeability of the inductor is measured as a function of the inductance, and the inductance becomes a measure of the number of particles collected by the filter.

SUMMARY OF THE DISCLOSURE

In one aspect of the present disclosure, an oil recirculation system for an engine is provided. The oil recirculation system includes a first conduit coupled to the engine to receive an oil therethrough and a second conduit coupled to the engine to supply the oil to the engine. The oil recirculation system further includes a filtering device disposed between the first conduit and the second conduit. The filtering device includes a first housing member defining a first chamber therein. The first chamber is in fluid communication with the first conduit. The filtering device further includes a second housing member removably coupled to the first housing member. The second housing member defines a second chamber therein. The second chamber is in fluid communication with the second conduit. The first chamber and the second chamber together define a passage to receive the oil therethrough. The filtering device further includes a filter member disposed in the passage to filter the oil flowing therethrough.

In another aspect of the present disclosure, a filtering device in an oil recirculation system of an engine is provided. The oil recirculation system includes a first conduit coupled to the engine to receive an oil therethrough and a second conduit coupled to the engine to supply the oil to the engine. The filtering device includes a first housing member defining a first chamber therein. The first chamber is in fluid communication with the first conduit. The filtering device further includes a second housing member removably coupled to the first housing member. The second housing member defines a second chamber therein. The second chamber is in fluid communication with the second conduit. The first chamber and the second chamber together define a passage to receive the oil therethrough. The filtering device further includes a filter member disposed in the passage to filter the oil flowing therethrough.

In yet another aspect of the present disclosure, a method of inspecting an oil of an engine is provided. The method includes receiving the oil from the engine and allowing the oil to pass through a filter member disposed between a first housing member and a second housing member of a filtering device. The filtering device is disposed between a first conduit and a second conduit coupled to the engine for circulating the oil. The method further includes detaching the first housing member from the second housing member periodically to inspect the filter member.

Other features and aspects of this disclosure will be apparent from the following description and the accompanying drawings.

DETAILED DESCRIPTION

Reference will now be made in detail to specific embodiments or features, examples of which are illustrated in the accompanying drawings. Wherever possible, corresponding or similar reference numbers will be used throughout the drawings to refer to the same or corresponding parts.

Figure 1:
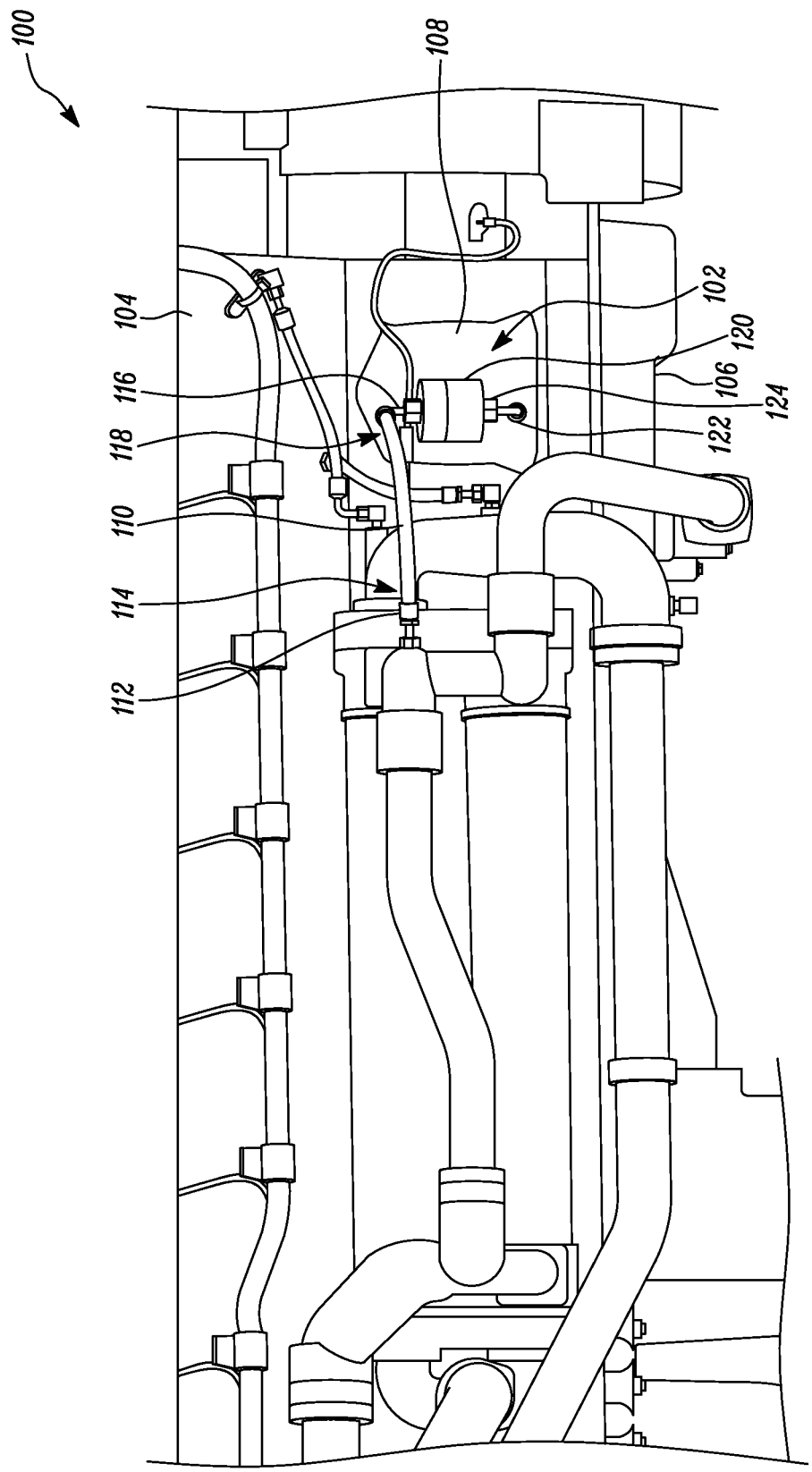
FIG. 1 is a partial side view of an engine having an oil recirculation system, according to an embodiment of the present disclosure.

FIG. 1 illustrates a partial side view of an engine 100 having an oil recirculation system 102, according to an embodiment of the present disclosure. In the illustrated embodiment, the engine 100 is used in a generator set. The generator set may be configured to supply an electric power in locations where utility power is not available or when backup electric power is required. Specifically, in applications such as telecommunications, hospitals and data processing centers, the generator set may be permanently installed on a ground surface near the respective locations. The generator set includes the engine 100 and a generator (not shown) operatively coupled to the engine 100 to generate the electric power. The oil recirculation system 102 is configured to recirculate oil within the engine 100 to lubricate various moving components, such as a crankshaft, one or more cam shafts and one or more pistons associated with the engine 100. The oil recirculation system 102 of the present disclosure may also be embodied in engines used in machines, such as on-highway and off-highway vehicles.

Referring to FIG. 1, a v-type engine is shown as an example for illustration purpose of the present disclosure. However, it may be contemplated that the engine 100 may include a single cylinder or a plurality of cylinders arranged in various configurations such as, an inline configuration or a rotary configuration. The engine 100 may be run by fuels such as, for example, diesel, gasoline, a gaseous fuel, or a combination thereof.

The engine 100 includes a cylinder block 104 for defining one or more cylinders (not shown) therein. The engine 100 may further include a cylinder head (not shown) mounted on the cylinder block 104. The cylinder head may define one or more inlet ports for receiving ambient air and one or more outlet ports for exiting exhaust gas from the cylinders. Each of the cylinders may further include a piston slidably disposed therein. The pistons may be further connected to the crankshaft for producing a rotary power. The crankshaft may be further coupled to the generator for converting the rotary power into the electric power.

The engine 100 further includes an oil pan 106 for containing the oil within the engine 100. The oil may be supplied to various moving components of the engine 100 by an oil pump disposed within the oil pan 106. One or more filters may be disposed within the oil pan 106 to filter the oil before the oil is supplied to such various moving components. Various lubrication systems, such as a splash and circulating pump system, a splash and pressure system, and a full force-feed system may be employed in the engine 100. After a prolonged period of operation of the engine 100, debris may get added in the oil. Hence, the oil is periodically changed by a customer or an operator to improve efficiency of operation of the engine 100 even after the prolonged period of operation thereof.

In the illustrated embodiment, the oil recirculation system 102 is disposed adjacent to a side wall 108 of the cylinder block 104. The oil pan 106 is coupled to the side wall 108 of the cylinder block 104 to contain the oil therein. In other embodiments, the oil recirculation system 102 may be disposed at any location in the engine 100 or the generator set. The oil recirculation system 102 includes a first conduit 110 coupled to the engine 100 to receive the oil therethrough. In an example, the first conduit 110 may be a pipe or a hose. The first conduit 110 includes a first connecting member 112 disposed adjacent to a first end 114 thereof and a first coupling member 116 disposed adjacent to a second end 118 thereof. The first conduit 110 is coupled to the engine 100 via the first connecting member 112. The first connecting member 112 is configured to be fluidly coupled with a port (not shown) defined in the side wall 108 of the engine 100. The oil is received in the first conduit 110 through the port. It may be contemplated that the first connecting member 112 may be coupled to any location in the engine 100 to receive the oil in the first conduit 110. The first coupling member 116 is fluidly coupled to a filtering device 120 of the oil recirculation system 102. The filtering device 120 is described in detail herein below with reference to FIG. 2.

The oil recirculation system 102 further includes a second conduit 122 coupled to the engine 100 to supply the oil to the engine 100. The second conduit 122 is coupled between the filtering device 120 and the engine 100 such that the oil received in the first conduit 110 passes through the filtering device 120 and supplied back to the engine 100 through the second conduit 122. In an example, the second conduit 122 may be a pipe or a hose. The second conduit 122 includes a second connecting member (not shown) disposed adjacent to a first end (not shown) thereof and a second coupling member 124 disposed adjacent to a second end 126 (shown in FIG. 2) thereof. The second conduit 122 is coupled to the engine 100 via the second connecting member. The second connecting member is configured to be fluidly coupled with a port (not shown) defined in the side wall 108. The oil received in the second conduit 122 is supplied back to the engine 100 through the port. It may be contemplated that the second connecting member may be coupled to any location in the engine 100 to supply the oil to the engine 100. The second coupling member 124 is fluidly coupled to the filtering device 120 to receive the oil from the filtering device 120. Thus the filtering device 120 is disposed between the first conduit 110 and the second conduit 122 to circulate the oil to the engine 100. In an embodiment, the filtering device 120 may be further removably supported in the cylinder block 104 via a supporting member (not shown). The supporting member may be fastened to the side wall 108 via fastening members, such as bolts and nuts.

Figure 2:
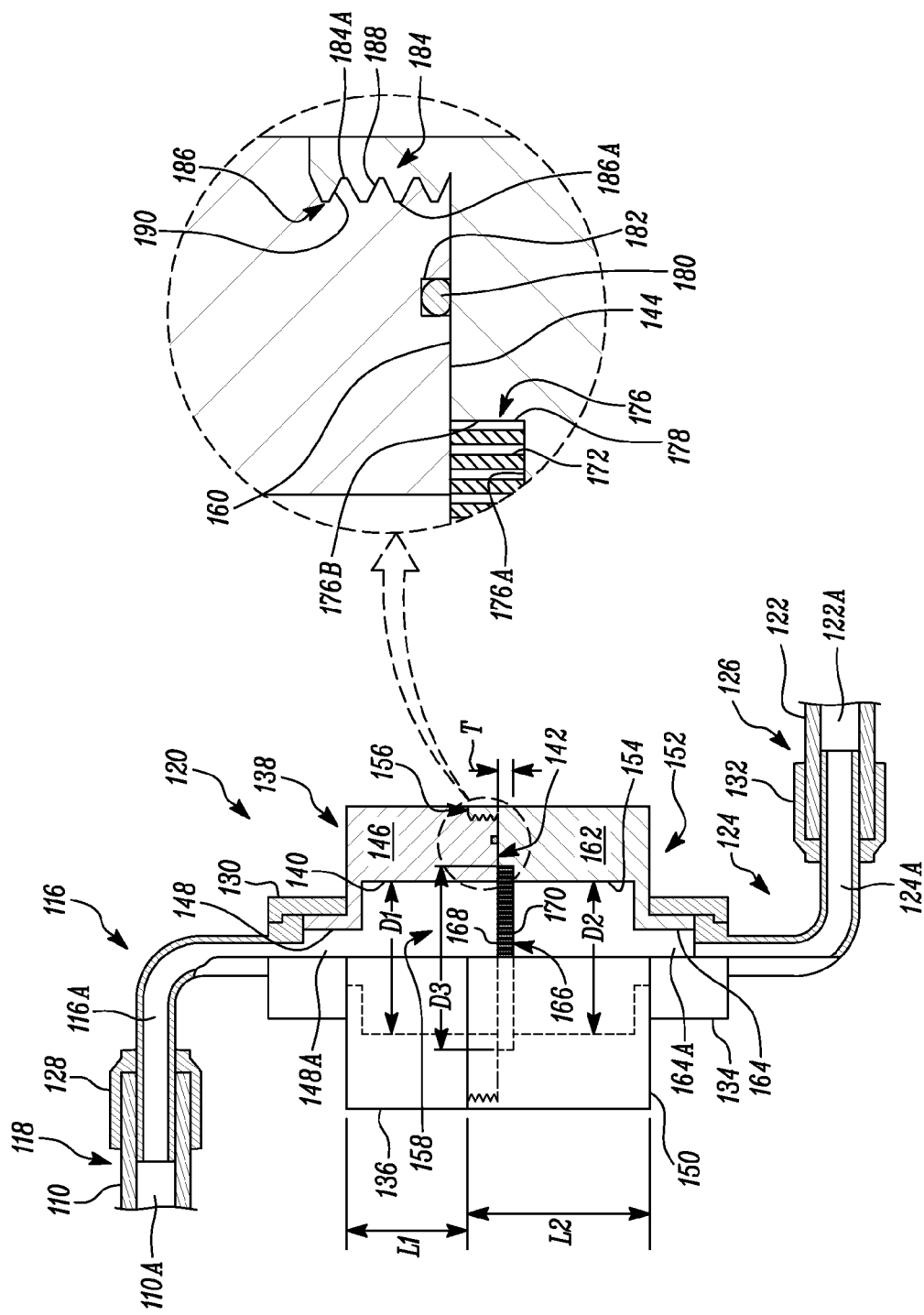
FIG. 2 is a partial sectional view of the oil recirculation system, according to an embodiment of the present disclosure.

FIG. 2 illustrates a partial sectional view of the oil recirculation system 102, according to an embodiment of the present disclosure. The first coupling member 116 includes a first coupling portion 128 configured to be coupled with the second end 118 of the first conduit 110. The first coupling portion 128 further configured to provide a fluid tight coupling between the first conduit 110 and the first coupling member 116. Thus an oil passage 110A defined by the first conduit 110 may be fluidly communicated with an oil passage 116A defined by the first coupling member 116. In an example, the second end 118 of the first conduit 110 may be press-fitted with the first coupling portion 128. In another example, the second end 118 of the first conduit 110 may be threadingly engaged with the first coupling portion 128 if the first conduit 110 is a pipe. In yet another example, the second end 118 of the first conduit 110 may be coupled to the first coupling portion 128 via a circlip member. The first coupling member 116 further includes a second coupling portion 130 configured to be coupled with the filtering device 120.

Similarly, the second coupling member 124 includes a first coupling portion 132 configured to be coupled with the second end 126 of the second conduit 122. The first coupling portion 132 further configured to provide a fluid tight coupling between the second conduit 122 and the second coupling member 124. Thus an oil passage 122A defined by the second conduit 122 may be fluidly communicated with an oil passage 124A defined by the second coupling member 124. The second coupling member 124 further includes a second coupling portion 134 configured to be coupled with the filtering device 120. In an embodiment, the second coupling member 124 and the first coupling member 116 may be similar in terms of shape, size and other dimensional specification. In such a case, a pair of one of the first coupling member 116 and the second coupling member 124 may be used for coupling the first and the second conduits 110, 122 with the filtering device 120.

The filtering device 120 includes a first housing member 136 fluidly coupled to the first conduit 110 via the first coupling member 116. In the illustrated embodiment, the first housing member 136 is a cylindrical body having a length 'L1'. However, in other embodiments, the first housing member 136 may have a cross sectional shape, such as a square, a rectangular, an elliptical, a polygonal, or any other shape known in the art. The first housing member 136 further includes a first end 138 configured to be coupled with the first conduit 110 via the first coupling member 116. The first housing member 136 further defines a first chamber 140 configured to be in fluid communication with the first conduit 110. The first chamber 140 extends between the first end 138 and a second end 142 of the first housing member 136. In the illustrated embodiment, the first chamber 140 may have a circular cross section defining an inner diameter 'D1'. However, in other embodiments, the first chamber 140 may have a cross sectional shape, such as a square, a rectangular, an elliptical, a polygonal, or any other shape known in the art. The first housing member 136 further includes a first mating surface 144 defined at the second end 142 thereof. The first mating surface 144 is defined by a wall 146 of the first housing member 136. In the illustrated embodiment, the first mating surface 144 is planar. However, in other embodiments, the first mating surface 144 may be non-planar.

The first housing member 136 further includes a first flange portion 148 adjacent to the first end 138 thereof. The first flange portion 148 extends vertically from the first end 138 of the first housing member 136. The first flange portion 148 is configured to be coupled to the second coupling portion 130 of the first coupling member 116. The first flange portion 148 is further integrally formed with the first housing member 136. In another embodiment, the first flange portion 148 may be a separate component coupled to the first end 138 of the first housing member 136. In an example, the first flange portion 148 may be press-fitted with the second coupling portion 130 of the first coupling member 116. In another example, the first flange portion 148 may be threadingly engaged with the second coupling portion 130 via a nut. In yet another example, the first flange portion 148 may be coupled with the second coupling portion 130 via a circlip member.

The first flange portion 148 further defines a first channel 148A configured to be in fluid communication with the first chamber 140 of the first housing member 136 and the first conduit 110. Specifically, the first channel 148A is configured to be in fluid communication with the oil passage 116A of the first coupling member 116 to further communicate with the first conduit 110.

The filtering device 120 further includes a second housing member 150 removably coupled to the first housing member 136. The second housing member 150 is further fluidly coupled to the second conduit 122 via the second coupling member 124. The second housing member 150 is a cylindrical body having a length 'L2'. In an embodiment, the length 'L1' and the length 'L2' may be equal. The second housing member 150 further includes a first end 152 configured to be coupled with the second conduit 122 via the second coupling member 124. The second housing member 150 further defines a second chamber 154 configured to be in fluid communication with the second conduit 122. The second chamber 154 extends between the first end 152 and a second end 156 of the second housing member 150. In the illustrated embodiment, the second chamber 154 may have a circular cross section defining an inner diameter 'D2'. The inner diameter 'D2' of the second chamber 154 may be equal to the inner diameter 'D1' of the first chamber 140. The second chamber 154 of the second housing member 150 and the first chamber 140 of the first housing member 136 are configured to together define a passage 158 for receiving the oil therethrough. The second housing member 150 further includes a second mating surface 160 defined adjacent to the second end 156 thereof. The second mating surface 160 is defined by a wall 162 of the second housing member 150. The second mating surface 160 is configured to abut the first mating surface 144 of the first housing member 136.

The second housing member 150 further includes a second flange portion 164 at the first end 152 thereof. The second flange portion 164 extends vertically from the first end 152 of the second housing member 150. The second flange portion 164 is configured to be coupled to the second coupling portion 134 of the second coupling member 124. The second flange portion 164 is further integrally formed with the second housing member 150. In another embodiment, the second flange portion 164 may be a separate component coupled to the first end 152 of the second housing member 150. The second flange portion 164 may be further coupled to the second coupling portion 134 of the second coupling member 124 similar to the way the first flange portion 148 is coupled to the second coupling portion 130 of the first coupling member 116.

The second flange portion 164 defines a second channel 164A configured to be in fluid communication with the second chamber 154 of the second housing member 150 and the second conduit 122. Specifically, the second channel 164A is configured to be in fluid communication with the oil passage 122A of the second coupling member 124 to further communicate with the second conduit 122.

The filtering device 120 further includes a filter member 166 disposed in the passage 158 defined by the first and second chambers 140, 154 to filter the oil flowing therethrough. The filter member 166 has a first surface 168 and a second surface 170 distal to the first surface 168. In the illustrated embodiment, the filter member 166 has a circular cross section defining an outer diameter 'D3'. The outer diameter 'D3' is greater than the inner diameters 'D1' and 'D2' of the first and second chambers 140, 154, respectively, such that the filter member 166 may be supported in at least one of the first and second housing members 136, 150. The filter member 166 further includes a plurality of pores 172 extending between the first surface 168 and the second surface 170 to allow the oil to flow therethrough. In the illustrated embodiment, size of each of the pores 172 varies from 60-80 microns. In various embodiments, the size of each of the pores 172 may be defined based on various parameters including, but not limited to, viscosity of the oil and size of debris to be filtered from the oil.

In the illustrated embodiment, the second housing member 150 includes a receiving portion 176 configured to removably receive the filter member 166 therein. The receiving portion 176 is defined at the second mating surface 160 around the second chamber 154. The receiving portion 176 includes a first engaging portion 176A configured to contact with the second surface 170 of the filter member 166 and a second engaging portion 176B configured to contact with an outer surface 178 of the filter member 166. The first mating surface 144 of the first housing member 136 is configured to contact with the first surface 168 of the filter member 166. Thus the filter member 166 is disposed between the first housing member 136 and the second housing member 150 along the passage 158 to allow the oil to flow therethrough. In an embodiment, two or more filter members 166 having different pore sizes may be arranged within the receiving portion 176. Further, the second engaging portion 176B has a thickness 'T' for receiving one or more filter members 166 within the receiving portion 176.

A sealing member 180 is disposed within an annular groove 182 defined in the first mating surface 144 of the first housing member 136. The sealing member 180 is further configured to be disposed between the first mating surface 144 and the second mating surface 160 to prevent leakage of oil from the filtering device 120. In an example, the sealing member 180 may be an O-ring. In another embodiment, the annular groove 182 may be defined on the second mating surface 160 to receive the sealing member 180 therein. In yet another embodiment, a liquid sealant or a sealant member, such as a gasket, may be disposed between the first mating surface 144 and the second mating surface 160 to prevent leakage of the oil from the filtering device 120.

The first housing member 136 further includes a step portion 184 defined adjacent to the second end 142 thereof. The step portion 184 may have an outer diameter smaller than an outer diameter of the first housing member 136. The step portion 184 is further configured to be removably engaged with a mating portion 186 defined adjacent to the second end 156 of the second housing member 150. The mating portion 186 has an inner surface 186A and defines the second mating surface 160 to contact with the first mating surface 144 defined by the step portion 184. The inner surface 186A of the mating portion 186 is further configured to engage with an outer surface 184A of the step portion 184.

In the illustrated embodiment, threads 188 are defined on the outer surface 184A of the step portion 184 to removably engage with corresponding threads 190 defined on the inner surface 186A of the mating portion 186. In various embodiments, the step portion 184 may be removably engaged with the mating portion 186 by a known clamping mechanism or a locking mechanism.

INDUSTRIAL APPLICABILITY

The present disclosure relates to the oil recirculation system 102 and a method 200 of inspecting the oil of the engine 100. The oil recirculation system 102 includes the filtering device 120 coupled to the engine 100 via the first conduit 110 and the second conduit 122. The oil is circulated through the filtering device 120 such that the filter member 166 disposed in the passage 158 may filter wear particles contained in the oil. A customer may disengage the first housing member 136 from the second housing member 150 to inspect the filter member 166 and to assess extent of wear particles in the oil.

Figure 3:
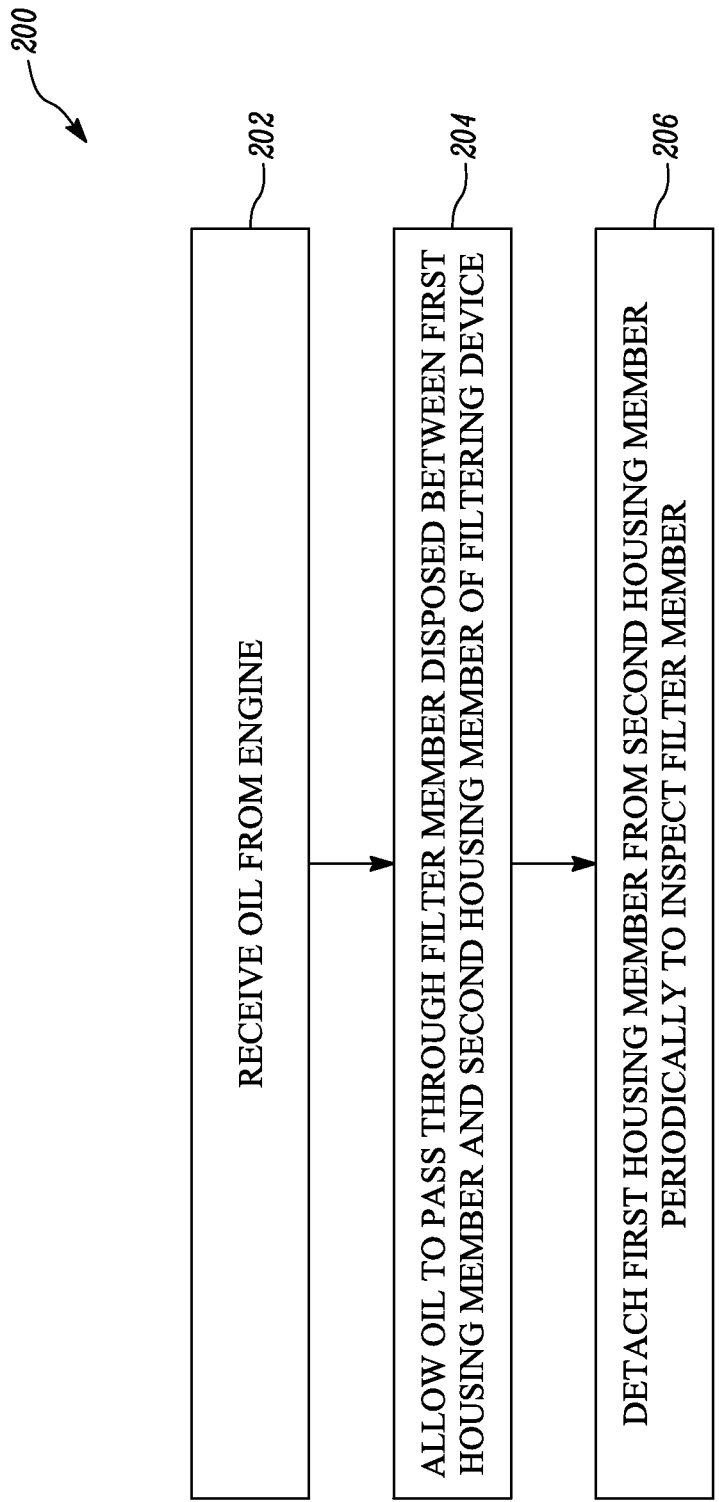
FIG. 3 is a flow chart of a method of inspecting an oil of the engine, according to an embodiment of the present disclosure.

FIG. 3 illustrates a flow chart of the method 200 of inspecting the oil, according to an embodiment of the present disclosure. At step 202, the method 200 includes receiving the oil from the engine 100. During operation of the engine 100, the oil may flow into the first conduit 110 via the first connecting member 112. The first conduit 110 may be coupled to the side wall 108 in such a way that the oil may flow into the first conduit 110 due to gravity. At step 204, the method 200 includes allowing the oil to pass through the filter member 166 disposed between the first and second housing members 136, 150. The oil received in the first conduit 110 may further pass through the passage 158 of the filtering device 120. The filtering device 120 is located below the first conduit 110 such that the oil may pass through the filter member 166 due to gravity. It may also be contemplated that the oil may pass through the filter member 166 due to a pressure at which the oil is supplied to various components of the engine 100. As the oil passes through the filter, the wear particle contained in the oil may be removed from the oil and accumulated in the filter member 166.

At step 206, the method 200 includes detaching the first housing member 136 from the second housing member 150 periodically to inspect the filter member 166. The step portion 184 of the first housing member 136 is threadingly engaged with the mating portion 186 of the second housing member 150. Thus the customer may quickly and easily disengage the first housing member 136 from the second housing member 150, when engine 100 is not in operation. Further, the filter member 166 may be easily removed from the receiving portion 176 to inspect the filter member 166 and to assess the extent of wear particles in the oil. In an embodiment, the method 200 further includes replacing the filter member 166 based on the inspection. In another embodiment, the filter member 166 may be cleaned and used multiple times.

Although the manufacturer recommends a defined period of time to change the oil in the engines, the customer can inspect quality of the oil in less time with the oil recirculation system 102. The filtering member 166 is designed in such a way that the customer can easily and quickly dismantle the filtering device 120 to inspect the filter member 166 and hence to assess the extent of wear particle in the oil. With the additional filtering device 120 apart from the filters disposed within the oil pan 106, oil may be used in the engine 100 for an extended period of time. Further, the customer may have various options to either replace the filter member 166 after a specific period of time or clean the filter member 166 and use multiple times.

While aspects of the present disclosure have been particularly shown and described with reference to the embodiments above, it will be understood by those skilled in the art that various additional embodiments may be contemplated by the modification of the disclosed systems and methods without departing from the spirit and scope of what is disclosed. Such embodiments should be understood to fall within the scope of the present disclosure as determined based upon the claims and any equivalents thereof.

What is claimed is:

1. An oil recirculation system for an engine comprising:
   a first conduit coupled to the engine to receive an oil therethrough;
   a second conduit coupled to the engine to supply the oil to the engine; and
   a filtering device disposed between the first conduit and the second conduit, the filtering device comprising:
      a first housing member defining a first chamber therein, the first chamber being directly connected with first conduit;
      a second housing member removably coupled to the first housing member, the second housing member defining a second chamber therein, the second chamber being directly connected with second conduit, wherein the first chamber and the second chamber together define a passage to receive the oil therethrough; and
      a filter member disposed in the passage to filter the oil flowing therethrough.

2. The oil recirculation system of claim 1 further comprising a first coupling member configured to be coupled with a first flange portion defined adjacent to a first end of the first housing member, wherein the first coupling member is further coupled to the first conduit.

3. The oil recirculation system of claim 2, wherein the first flange portion defines a first channel configured to be in fluid communication with the first chamber of the first housing member and the first conduit.

4. The oil recirculation system of claim 1 further comprising a second coupling member configured to be coupled with a second flange portion defined adjacent to a first end of the second housing member, wherein the second coupling member is further coupled to the second conduit.

5. The oil recirculation system of claim 4, wherein the second flange portion defines a second channel configured to be in fluid communication with the second chamber of the second housing member and the second conduit.

6. The oil recirculation system of claim 1, wherein:
   the first housing member defines a first mating surface adjacent to a second end thereof; and
   the second housing member defines a second mating surface adjacent to a second end thereof, the second mating surface configured to abut the first mating surface of the first housing member;
   wherein at least one of the first mating surface and the second mating surface comprises an annular groove configured to receive a sealing member therein.

7. The oil recirculation system of claim 6, wherein:
the first housing member comprises a step portion adjacent to the second end thereof; and
the second housing member comprises a mating portion adjacent to the second end thereof, the mating portion configured to be removably engaged with the step portion of the first housing member.

8. The oil recirculation system of claim 7 further comprising threads defined on an outer surface of the step portion to engage with corresponding threads defined on an inner surface of the mating portion.

9. The oil recirculation system of claim 1, wherein at least one of the first housing member and the second housing member comprises a receiving portion configured to removably receive the filter member therein.

10. The oil recirculation system of claim 1, wherein the filter member has a pore size varying from 60-80 microns.

11. A filtering device in an oil recirculation system of an engine, the oil recirculation system having a first conduit coupled to the engine to receive an oil therethrough and a second conduit coupled to the engine to supply the oil to the engine, the filtering device comprising:
a first housing member defining a first chamber therein, the first chamber being directly connected with first conduit;
a second housing member removably coupled to the first housing member, the second housing member defining a second chamber therein, the second chamber being directly connected with second conduit, wherein the first chamber and the second chamber together define a passage to receive the oil therethrough; and
a filter member disposed in the passage to filter the oil flowing therethrough.

12. The filtering device of claim 11 further comprising a first flange portion defined adjacent to a first end of the first housing member, the first flange portion defines a first channel configured to be in fluid communication with the first chamber of the first housing member and the first conduit.

13. The filtering device of claim 11 further comprising a second flange portion defined adjacent to a first end of the second housing member, the second flange portion defines a second channel configured to be in fluid communication with the second chamber of the second housing member and the second conduit.

14. The filtering device of claim 11, wherein:
the first housing member defines a first mating surface adjacent to a second end thereof; and
the second housing member defines a second mating surface adjacent to a second end thereof, the second mating surface configured to abut the first mating surface of the first housing member;
wherein at least one of the first mating surface and the second mating surface comprises an annular groove configured to receive a sealing member therein.

15. The filtering device of claim 14, wherein:
the first housing member comprises a step portion adjacent to the second end thereof; and
the second housing member comprises a mating portion adjacent to the second end thereof, the mating portion configured to be removably engaged with the step portion of the first housing member.

16. The filtering device of claim 15 further comprising threads defined on an outer surface of the step portion to engage with corresponding threads defined on an inner surface of the mating portion.

17. The filtering device of claim 11, wherein at least one of the first housing member and the second housing member comprises a receiving portion configured to removably receive the filter member therein.

18. The filtering device of claim 11, wherein the filter member has a pore size varying from 60-80 microns.

19. A method of inspecting an oil of an engine, the method comprising:
receiving the oil from the engine;
allowing the oil to pass through a filter member disposed between a first housing member and a second housing member of a filtering device, the filtering device disposed between a first conduit directly connected to the first housing member, and a second conduit directly connected to the second housing member, both coupled to the engine for circulating the oil; and
detaching the first housing member from the second housing member periodically to inspect the filter member.

20. The method of claim 19 further comprising replacing the filter member based on the inspection.

* * * * *